US011241671B2

(12) United States Patent
Petruska et al.

(10) Patent No.: US 11,241,671 B2
(45) Date of Patent: Feb. 8, 2022

(54) MONOLITHIC COMPOSITE PHOTOCATALYSTS

(71) Applicants: Melissa A. Petruska, Newtown, CT (US); Trevor E. James, Plantsville, CT (US); James D. Carruthers, Reno, NV (US); Peter C. Van Buskirk, Newtown, CT (US); Jeffrey F. Roeder, Brookfield, CT (US)

(72) Inventors: Melissa A. Petruska, Newtown, CT (US); Trevor E. James, Plantsville, CT (US); James D. Carruthers, Reno, NV (US); Peter C. Van Buskirk, Newtown, CT (US); Jeffrey F. Roeder, Brookfield, CT (US)

(73) Assignee: Sonata Scientific LLC, Danbury, CT (US)

( * ) Notice: Subject to any disclaimer, the term of this patent is extended or adjusted under 35 U.S.C. 154(b) by 116 days.

(21) Appl. No.: 16/680,495

(22) Filed: Nov. 12, 2019

(65) Prior Publication Data
US 2020/0101440 A1 Apr. 2, 2020

Related U.S. Application Data

(63) Continuation-in-part of application No. 16/212,663, filed on Dec. 6, 2018, and a continuation-in-part of application No. 16/147,536, filed on Sep. 28, 2018.
(Continued)

(51) Int. Cl.
*B01J 21/04* (2006.01)
*B01J 21/06* (2006.01)
(Continued)

(52) U.S. Cl.
CPC ............. *B01J 21/063* (2013.01); *A61L 2/084* (2013.01); *A61L 2/10* (2013.01); *A61L 2/16* (2013.01);
(Continued)

(58) Field of Classification Search
CPC . B01J 21/063; B01J 21/04; B01J 21/06; B01J 21/066; B01J 21/08; B01J 21/12; B01J 23/10; B01J 35/004; B01J 35/006; B01J 35/023; B01J 35/04; B01J 35/08; B01J 35/1014; B01J 35/1019; B01J 35/1023; B01J 35/1038; B01J 35/1042; B01J 35/1047; B01J 35/1061; A61L 2/084; A61L 2/10; A61L 2/16
See application file for complete search history.

(56) References Cited

U.S. PATENT DOCUMENTS 5,658,841 A * 8/1997 Tanaka ................... B01J 35/002
502/242
5,780,380 A * 7/1998 Endoh .................... B01J 35/004
502/300

(Continued)

*Primary Examiner* — Cam N. Nguyen
(74) *Attorney, Agent, or Firm* — Gregory Stauf

(57) ABSTRACT

Monolithic composite photocatalysts for fluid purification, chemical transformations, and surface sterilization are disclosed. The monolithic composite photocatalysts comprise a photoactive nanocrystal component and a non-photoactive porous support. Photocatalytic fluid purification systems that contact an impurity-containing fluid with the subject monolithic composite photocatalysts are also disclosed.

25 Claims, 10 Drawing Sheets

Related U.S. Application Data

(60) Provisional application No. 62/760,428, filed on Nov. 13, 2018, provisional application No. 62/595,261, filed on Dec. 6, 2017, provisional application No. 62/595,261, filed on Dec. 6, 2017, provisional application No. 62/564,408, filed on Sep. 28, 2017.

(51) Int. Cl.
| | |
|---|---|
| *B01J 21/08* | (2006.01) |
| *B01J 21/12* | (2006.01) |
| *B01J 23/10* | (2006.01) |
| *B01J 35/00* | (2006.01) |
| *B01J 35/02* | (2006.01) |
| *B01J 35/04* | (2006.01) |
| *B01J 35/08* | (2006.01) |
| *B01J 35/10* | (2006.01) |
| *A61L 2/08* | (2006.01) |
| *A61L 2/10* | (2006.01) |
| *A61L 2/16* | (2006.01) |
| *B82Y 35/00* | (2011.01) |
| *B82Y 40/00* | (2011.01) |

(52) U.S. Cl.
CPC ........ *B01J 35/004* (2013.01); *B01J 35/006* (2013.01); *B01J 35/023* (2013.01); *B01J 35/04* (2013.01); *B01J 35/08* (2013.01); *B01J 35/1014* (2013.01); *B01J 35/1019* (2013.01); *B01J 35/1023* (2013.01); *B01J 35/1061* (2013.01); *B82Y 35/00* (2013.01); *B82Y 40/00* (2013.01)

(56) References Cited

U.S. PATENT DOCUMENTS

| | | | | |
|---|---|---|---|---|
| 7,795,173 | B2* | 9/2010 | Vanderspurt | B01J 21/063 |
| | | | | 502/350 |
| 8,283,277 | B2* | 10/2012 | Seeber | C09C 1/3684 |
| | | | | 502/159 |
| 8,673,810 | B2* | 3/2014 | Zhao | C01G 23/053 |
| | | | | 502/350 |
| 9,018,122 | B2* | 4/2015 | Mao | C01G 23/047 |
| | | | | 502/100 |
| 9,040,489 | B2* | 5/2015 | Labuz | A61L 12/088 |
| | | | | 514/27 |
| 9,868,109 | B2* | 1/2018 | Cheng | B01J 21/063 |
| 2005/0239644 | A1* | 10/2005 | Zhu | B01J 35/004 |
| | | | | 502/350 |
| 2009/0104086 | A1* | 4/2009 | Zax | A61L 2/10 |
| | | | | 422/121 |
| 2013/0153483 | A1* | 6/2013 | Morazzoni | B01J 35/1071 |
| | | | | 210/263 |
| 2014/0256534 | A1* | 9/2014 | Gao | B01J 23/66 |
| | | | | 502/5 |
| 2015/0111725 | A1* | 4/2015 | Van Buskirk | B01J 21/063 |
| | | | | 502/200 |
| 2015/0376441 | A1* | 12/2015 | Guldin | G02B 27/0006 |
| | | | | 428/220 |
| 2016/0346763 | A1* | 12/2016 | Wahab | B01J 37/035 |
| 2017/0056873 | A1* | 3/2017 | Jones | C02F 1/32 |
| 2017/0274364 | A1* | 9/2017 | Idriss | B01J 23/48 |
| 2020/0298214 | A1* | 9/2020 | Khan | B01J 35/0033 |
| 2020/0360857 | A1* | 11/2020 | Van Buskirk | B01J 35/004 |

\* cited by examiner

MONOLITHIC COMPOSITE PHOTOCATALYSTS

CROSS REFERENCE TO RELATED APPLICATIONS

This application is a U.S. Utility application taking priority from U.S. Provisional Application No. 62/564,408 "Photocatalytic Fluid Purification Systems" filed Sep. 28, 2017, U.S. Provisional Application No. 62/595,261 "Photocatalytic Surface Systems", filed Dec. 6, 2017, U.S. Provisional Patent Application No. 62/760,428 "Monolithic Composite Photocatalyst" filed Sep. 13, 2108, U.S. Utility patent application Ser. No. 16/147,536 "Photocatalytic Fluid Purification Systems" filed Sep. 28, 2018 and from U.S. Utility patent application Ser. No. 16/212,663 "Photocatalytic Surface Systems" filed Dec. 6, 2018 all herein incorporated by reference.

This invention was made with government support under contracts from the National Science Foundation, NSF Award #1721968, and US Department of Agriculture, USDA Award #2018-33610-28231. The government has certain rights in the invention.

BACKGROUND

Field of the Invention

The present disclosure relates to a $TiO_2$-based monolithic composite photocatalyst that is useful for the mineralization of organic volatile organic compounds and gaseous organic compounds (e.g., ethylene) to $CO_2$ and $H_2O$. The monolithic composite photocatalysts may also be used to mineralize organic species in water. The monolithic composite photocatalysts are also useful as antimicrobial agents for airborne pathogens or microbe-contaminated surfaces, including plankton bacteria, bacterial spores, viruses, and fungal spores. These monolithic composite photocatalysts may also be used to photocatalyze chemical transformations. The disclosure additionally relates to the apparatus utilizing such monolithic composite photocatalysts for the mitigation of microbes, volatile organic materials and other environmental contamination, and the chemical transformation of different chemical reagents. It also relates to formulations for antimicrobial surface coatings utilizing said monolithic composite photocatalysts.

REFERENCES

M. Anpo, T. Shima, S. Kodama, Y. Kubokawa, "Photocatalytic hydrogenation of $CH_3CCH$ with $H_2O$ on small-particle $TiO_2$: Size quantization effects and reaction intermediates." *J. Phys. Chem.* 1987, 91, 4305-4310.

M. Anpo and M. Takeuchi, "The design and development of highly reactive titanium oxide photocatalysts operating under visible light irradiation." *J. Catalysis* 2003, 216, 505-516.

H. Yamashita, Y. Ichihashi, M. Anpo, M. Hashimoto, C. Louis, M. Che, "Photocatalytic decomposition of NO at 275 K on Titanium Oxides included within Y-zeolite cavities: The structure and role of the active sites." *J. Phys. Chem.* 1996, 100, 16041-16044.

M. Takeuchi, M. Hidaka, M. Anpo, "Efficient removal of toluene and benzene in gas phase by the TiO2/Y-zeolite hybrid photocatalyst." *J. Hazardous Materials* 2012, 237-238, 133-139.

T. Szymanski and J. Lockemeyer, "Catalyst Carrier." U.S. Pat. No. 5,733,840.

S.-E. Park, J.-S. Hwang, J.-S. Chang, J.-M. Kim, D. S. Kim, H. S. Chai, "Titania Photocatalyst and Its Preparing Method." U.S. Pat. No. 6,566,300.

L. Davydov, P. A. France, P. G. Smirniotis, "Photocatalytic Degradation of Organic Compounds." U.S. Pat. No. 6,585,863.

T. Morikawa, Y. Taga, T. Nakamura, Y. Fukushima, "Photocatalytic Substance." U.S. Pat. No. 6,680,277.

B. Setlow and P. Setlow, "Role of DNA repair in *Bacillus subtilis* spore resistance." *J. Bacteriol.* 1996, 1783486-, 3486-3495.

B. Djouiai, J. E. Thwaite, T. R. Laws, F. M. Commichau, B. Setlow, P. Setlow, R. Moeller, "Role of DNA repair and protective components in *Bacillus subtilis* spore resistance to inactivation by 400 nm blue light." *Appl. Environ. Microbiol.* 2018, 84, e01604-18.

The prevalence of volatile organic chemicals (VOCs) in industrial, commercial, and residential areas plays a significant role in indoor air quality (IAQ) and the health and quality of life of the occupants working and living in these spaces. Various methods for improving IAQ and reducing these noxious species have been developed depending on the space of interest, with some environments requiring expensive ventilation and conditioned make-up air units and other areas employing smaller, cost-effective, portable solutions. One approach to removing VOCs from the air is through photocatalysis, a process that uses light to create electron-hole pairs in a semiconductor, which then interact at the surface to form reactive oxygen species (ROS), such as OH. and $O_2^-$, that degrade the target compounds, eventually producing $CO_2$ and $H_2O$ in a process called mineralization. The wavelength of light to effect this reaction depends on the semiconductor of choice.

The need for clean drinking water cannot be overstated. Nearly 800 million people have limited or no access to clean, potable water. There are a wide variety of contaminants, including human and animal sourced pathogens (e.g., bacteria like *E. coli* and cholera and viruses like hepatovirus that causes hepatitis), heavy metals (e.g., arsenic), pharmaceuticals, and organic solvents. Each location may provide a unique combination of contaminants, so there is no "one size fits all" solution, but there are also many commonalities. Aside from the humanitarian aspect of this situation, the socio-economic costs include reduced productivity due to illness, increased burden on already strained health systems, and over-use of existing water supplies. The latter issue is beginning to impact even highly developed economies.

In addition to mineralizing VOCs, gaseous organic compounds, and organic species, photocatalysis may also be used as an antimicrobial approach. Society is faced with increasing threats from harmful microbes, including bacteria, viruses, spores and bacteria-comprised biofilms. Healthcare associated infections (HAIs) are a major problem that threaten life and increase costs of healthcare. The CDC estimates that in the U.S. there are 1.7 million hospital-associated infections annually, contributing to 99,000 deaths. In addition to airborne contamination, another primary transmission mode for these infections involves contact with contaminated surfaces, where bacteria and viruses can reside for days or even weeks on touch surfaces near the patient. Methicillin resistant *Staphylococcus aureus* (MRSA), *Clostridium difficile* (*C. difficile*), and other multiple drug resistant organisms (MDROs) are particularly dangerous and stubborn contagions that may reside on surfaces close to a patient. Many types are difficult to attack with antibiotics, and antibiotic resistance is spreading to Gram-negative bacteria that can infect people outside the hospital.

Outside the healthcare environment, there are a similar and increasing range of opportunistic mass-infections as evidenced by recent Norovirus outbreaks on cruise ships. These outbreaks may be spread by viruses, bacteria and spores that propagate both airborne and on surfaces.

It is well known that many standard disinfecting regimens (typically liquids comprised of bleach or hydrogen peroxide) may leave a residual contagion on a surface, which is known as "bioburden". Bioburden comprises biofilm or planktonic species residing at a surface that is nominally 'clean'. Its presence may be due to the failure of hospital staff to follow standard procedures; species with exceptional physical, chemical, and biological robustness; or a combination thereof. There are several disinfectant treatments that are receiving considerable attention as ways to augment liquid treatments. UV-C radiation, ozone, and disinfectant vapors or mists are known to be very effective but are highly hazardous and are only viable when a hospital room has been vacated.

Antimicrobial, or 'self-sterilizing', surfaces are highly desirable to complement standard cleaning. These surfaces act continuously, and ideally, they should have a high killing efficiency for a broad range of bacteria, viruses, and spores yet be non-toxic to humans.

Titanium dioxide (titania, $TiO_2$) is the archetypal photocatalyst because of its highly oxidizing properties when irradiated with UV light, insolubility in water, low cost, and low toxicity, among other attributes. Photocatalysis using $TiO_2$ has received interest for purifying gases and fluids, in particular air and water, via oxidizing chemical reactions at its surface, and it has also been explored as a strategy for killing pathogens in fluids, including air and water, and on surfaces.

Photocatalysis is typically achieved by illumination with a low or medium pressure UV lamp, or in some cases a Xenon lamp, irradiating the front surface of a bulk ceramic- or powder-based titania surface, i.e., from the direction of the medium that is targeted to be purified. UV light-emitting diodes (LEDs) have also been employed, although these devices typically have very short product lifetimes and are unreliable. Photocatalysis utilizing titanium dioxide is typically excited by illumination in the UV or near UV 240-400 nm spectral region.

The chemical activation at the surface of a photocatalyst originates with the formation of electron-hole pairs that arise from optical stimulation. Activation at the surface typically has a finite lifetime that is limited by charge separation and recombination of electron-hole pairs. Mitigation of these effects has been investigated primarily via chemical modification of the titania particles, although there has been no consensus in technical approach for manufacturing practical photocatalyst materials and systems.

A wide variety of titania-based materials, doping schemes, and physical configurations have been proposed to enhance and utilize photocatalysis at $TiO_2$ surfaces. Despite decades of research, low mineralization quantum yields, incomplete conversion of reactants, and catalyst fouling hinder widespread adoption of this technology for purification of air, fluids, and surfaces. The inventors of the present invention believe that several technical and economic factors have reduced the utility, effectiveness, and commercial viability of current photocatalytic air purification systems.

Much current research centers around the synthesis of $TiO_2$ and its analogues as bulk powders, which comprise aggregates of nanometer-scale (>10 nm) particles. For example, a commercial $TiO_2$, Evonik P-25, consists of approximately 30 nm $TiO_2$ nanocrystals agglomerated into larger aggregates. Useful implementation of these powders into systems for purifying air, fluids, and surfaces requires the support of these powders on macroscopic surfaces or the formation of these $TiO_2$-based materials into macroscopic articles through, e.g., pelleting or extruding processes. Often processes used to support the catalyst result in the degradation in performance of the photocatalyst compared to bulk powder. These supported powders may also suffer from attrition, leading to a decrease in performance and an increased amount of loose residue that may cause blockages and pressure drops in systems over time. Similarly, bulk pelleting can lead to reduced performance because of the inability of light to be transmitted through to the interior of the article, reducing efficiency and adding cost by photocatalytically utilizing only a small layer on the surface of the pellet or extrudate.

Bulk $TiO_2$-based powders are insoluble in water and other common solvents, and homogeneous dispersions rely on reducing the agglomerate size to aggregates that more readily suspend (not dissolve) in solvents. $TiO_2$ nanocrystals synthesized with surface capping groups may be prepared and easily dispersed; however, as photocatalysis is a surface effect, the challenge is to achieve sufficient available reactive sites on the $TiO_2$ nanocrystal surface for reactive oxygen species to be generated and to react with impurities in the fluid while remaining dispersed in the fluid or on a surface.

The monolithic composite photocatalysts of the present invention may be formed in a variety of configurations also identified in the present invention, thereby enabling a range of photocatalytic purification and antimicrobial surfaces and devices.

The monolithic composite photocatalysts of the present invention may also be used to catalyze certain chemical transformations that may be difficult to achieve with current catalyst schemes or may operate at reduced temperatures and/or pressures compared to current solutions.

$TiO_2$ particles have been synthesized directly on the surface of solid supports and used for the degradation of organic compounds. $TiO_2$ nanocrystals greater than 5 nm have been synthesized on the external surface of zeolites. $TiO_2$ particles, 0.5-5 nm have been synthesized in the micropores of zeolites using citric acid. It was claimed that the $TiO_2$ particles remain small because they reside in the micropores of the zeolite supports (micropores are defined as having a pore size less than 2 nm). $TiO_2$ has been added to mesoporous $Al_2O_3$ at loadings up to 10% to improve crush strength and abrasion resistance with no discussion or claims of photocatalytic properties of the materials. Zeolite and mesoporous molecular sieves have been doped with transition metals and then combined with photocatalysts for visible light activation.

The subject invention may be embodied in the following examples that are by no means restrictive but are intended to illustrate the invention. It will be clear that the described invention is well adapted to achieve the purposes described above, as well as those inherent within. The citation of any publication is for its disclosure prior to the filing date and should not be construed as an admission that the present invention is not entitled to antedate such publication by virtue of prior invention. Numerous other changes may be made which will readily suggest themselves to those skilled in the art and which are encompassed both in the spirit of the disclosure above and the appended claims.

SUMMARY OF THE INVENTION

The present disclosure relates to a $TiO_2$-based monolithic composite photocatalyst that is useful for the mineralization of organic volatile organic compounds and gaseous organic compounds (e.g., ethylene) to $CO_2$ and $H_2O$. The monolithic composite photocatalysts may also be used to mineralize organic species in water. The monolithic composite photocatalysts are also useful as antimicrobial agents for airborne pathogens or microbe-contaminated surfaces comprising plankton bacteria, bacterial spores, viruses, and fungal spores. These monolithic composite photocatalysts may also be used to photocatalyze chemical transformations.

DETAILED DESCRIPTION OF THE INVENTION, AND PREFERRED EMBODIMENTS THEREOF

Figure 1:
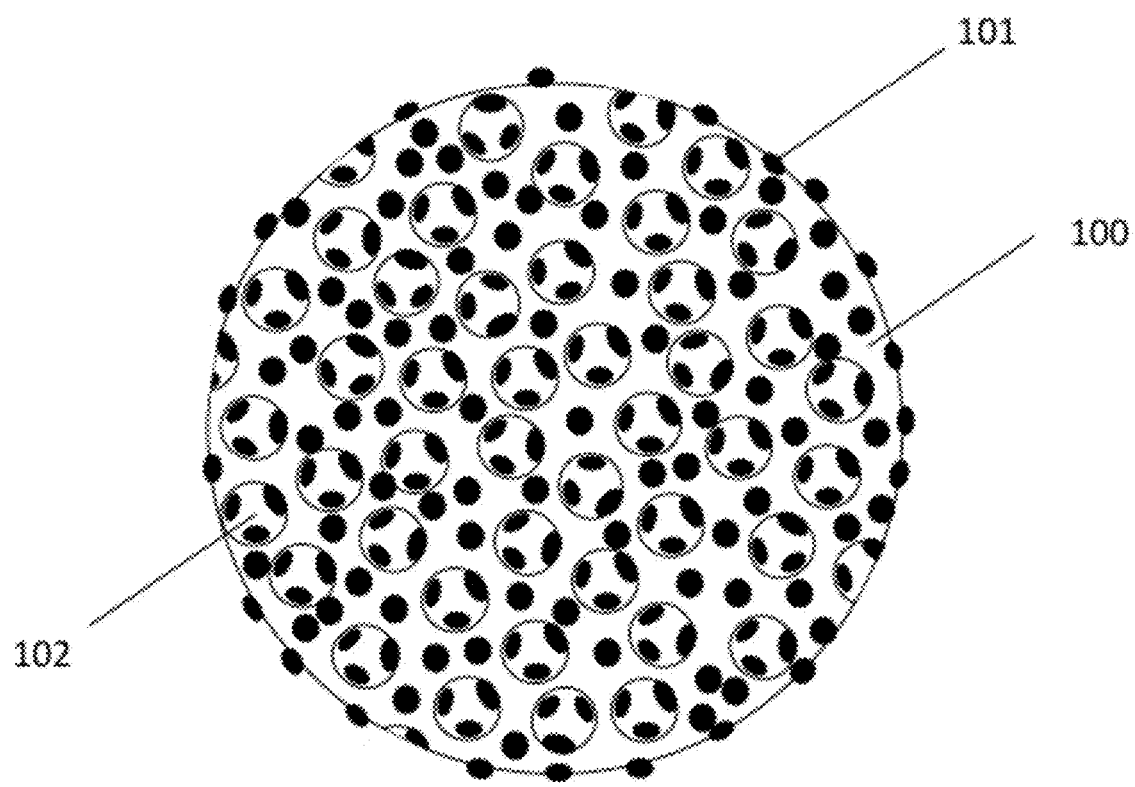
FIG. 1 shows a monolithic composite photocatalyst.

In one aspect, the disclosure relates to a monolithic composite photocatalyst (FIG. 1) comprising a non-photoactive porous support 100 for titania or titania-based photoactive nanocrystals 101. The photoactive nanocrystals may be dispersed within pores of the support 102 as well as on the surface. The monolithic composite photocatalyst of the present disclosure may have characteristics comprising those shown below:

(a) greater than 90% small, discrete photoactive nanocrystals or photoactive nanocrystal aggregates with size less than or equal to 5 nm;
(b) Monolithic composite photocatalyst $N_2$ BET surface area in the range 10-900 $m^2/g$, preferably 20-800 $m^2/g$, and most preferably 90-600 $m^2/g$;
(c) Mesopores of the monolithic composite photocatalyst in the range 2-50 nm, preferably 4-45 nm, and most preferably 6-40 nm.
(d) Photoactive nanocrystal loading 1-25% by mass, preferably 5-22%, most preferably 10-20%.

In another aspect, the disclosure relates to a monolithic composite photocatalyst comprising photoactive nanocrystals and a non-photoactive porous support for the photoactive nanocrystals, said photoactive nanocrystals comprising titania or titania-based nanocrystals and an inorganic sensitizer, and said monolithic composite photocatalyst having the following characteristics. The monolithic composite photocatalyst of the present disclosure may have characteristics comprising those shown below:

(a) greater than 90% discrete photoactive nanocrystals or photoactive nanocrystal aggregates with sizes less than or equal to 5 nm;
(b) monolithic composite photocatalyst $N_2$ BET surface area in the range 10-900 $m^2/g$;
(c) mesopores in the range 2-50 nm;
(d) Photoactive nanocrystal loading 1-30% by mass.

In another aspect, the disclosure relates to a fluid or gas purification apparatus and/or antimicrobial system comprising a monolithic composite photocatalyst of the present disclosure, arranged for contacting the impurity stream under conditions that mineralize the impurities using said monolithic composite photocatalyst.

A further aspect of the disclosure relates to a fluid or gas apparatus comprising a monolithic composite photocatalyst of the present disclosure for effecting a chemical transformation using said monolithic composite photocatalyst.

A further aspect of the disclosure relates to a solution that may be deposited as a robust antimicrobial coating on a variety of surfaces comprising the monolithic composite photocatalyst of the present disclosure.

Other aspects, features and embodiments of the disclosure will be more fully apparent from the ensuing description and appended claims.

As used herein and in the appended claims, mineralization of an organic species means conversion of the organic species to $CO_2$ and $H_2O$. Mineralization of an organic species containing nitrogen, sulfur, halides, and the like will also generate, in addition to $CO_2$ and $H_2O$, small molecule compounds (e.g., mineral acids) related to these functional moieties.

As used herein and in the appended claims, fluid refers to a gas or liquid, including air and water.

As used herein and in the appended claims, monolithic composite photocatalyst refers to a titania-based photoactive component and a non-photoactive porous support that may comprise powders and macroscopic articles having monolith, block, brick, bar, disc, columnar, honeycomb, channeled block, fibrous wool, felt, fabric, sponge, mat, particulate, tablet, pellet, extrudate, and bead forms, and the like.

As used herein and in the appended claims, photoactive nanocrystals are the titania or titania-based component of the monolithic composite photocatalyst that when activated with light produce electron-hole pairs that generate reactive oxygen species.

As used herein and in the appended claims, non-photoactive porous support is a mesoporous catalyst carrier that does not generate electron-hole pairs when stimulated with UV or visible light. The photoactive nanocrystals are supported on the non-photoactive support.

As used herein and in the appended claims, photoactive nanocrystals refer to the titania, the titania-based, or the titania-inorganic-sensitizer nanocrystals present as discrete particles or small aggregates of the monolithic composite photocatalyst where at least 90% of these photoactive nanocrystals are smaller than 5 nm, as determined from transmission electron microscopy (TEM) imaging.

As used herein and in the appended claims, discrete photoactive nanocrystals refer to nanocrystals where at least 90% of the photoactive nanocrystals are individual particles less than 5 nm or small agglomerates of photoactive nanocrystals less than 5 nm, as determined from TEM imaging.

As used herein and in the appended claims, titania-based photoactive nanocrystals are photoactive nanocrystals comprising at least 75% titania. The balance can include lanthanide or transition metal dopants, noble metals, and/or non-metal dopants.

As used herein and in the appended claims, a sensitizer is a molecule or compound that may be activated with light to generate electrons and/or holes that interact with the titania in the monolithic composite photocatalyst to enhance mineralization efficiencies. In schemes where the sensitizer has a narrower bandgap than the titania, the sensitizer absorbs light at a longer wavelength, generating electrons and holes that are injected into the titania, improving the photocatalytic response at longer wavelengths of light.

As used herein and in the appended claims, monolithic composite photocatalyst $N_2$ BET surface area is the value of surface area determined from BET (Brunauer Emmett Teller) analysis of $N_2$ isotherms collected at 77 K.

As used herein and in the appended claims, mesopore size of the monolithic composite photocatalyst is determined from BJH (Barrett, Joyner. and Halenda) analysis or from the cylindrical pore, NLDFT (non-localized density functional theory) equilibrium model of $N_2$ isotherms collected at 77 K.

As used herein and in the appended claims, macroporous refers to a porous material with pore size smaller than 2 nm.

As used herein and in the appended claims, mesoporous refers to a porous material with pore size 2-50 nm.

As used herein and in the appended claims, photoactive nanocrystal or nanocrystal aggregate sizes refer to either the major axis or minor axis of an ellipsoid, where in general the dimensions of the photoactive nanocrystals of the subject invention are less than or equal to 5 nm.

As used herein and in the appended claims, photoactive nanocrystal loading refers to the mass of the photoactive nanocrystal component ratioed to the mass of the entire monolithic composite photocatalyst, expressed as a percent.

As used herein and in the appended claims, the attrition is a measure of the particle size reduction of the monolithic composite photocatalyst when subjected to the test method described by ASTM D5757, "Standard Test Method for Determination of Attrition of FCC Catalysts by Air Jets." Briefly, air of a known flow rate is passed through an orifice plate. The monolithic composite photocatalyst particles interact with the air stream and other monolithic composite photocatalyst particles. Collected fines are weighted periodically to determine the attrition rate (wt %/h).

As used herein and in the appended claims, substantially organic-free indicates <2% carbon residue detected via elemental analysis on monolithic composite photocatalysts.

As used herein and in the appended claims, matrix refers to the liquid system with which the monolithic composite photocatalyst is mixed for coating purposes.

The present disclosure relates to a monolithic composite photocatalyst that is useful for the mineralization of organic volatile organic compounds in air, organic gaseous compounds, and organic compounds in water to $CO_2$ and $H_2O$. The monolithic composite photocatalysts are also useful as antimicrobial agents for airborne pathogens. This disclosure also relates to methods for using these monolithic composite photocatalysts.

The monolithic composite photocatalyst of the present disclosure is useful for the mineralization of VOCs in single component and multicomponent air streams. It is also useful for the mineralization of ethylene and other gaseous organic compounds.

Figure 2:
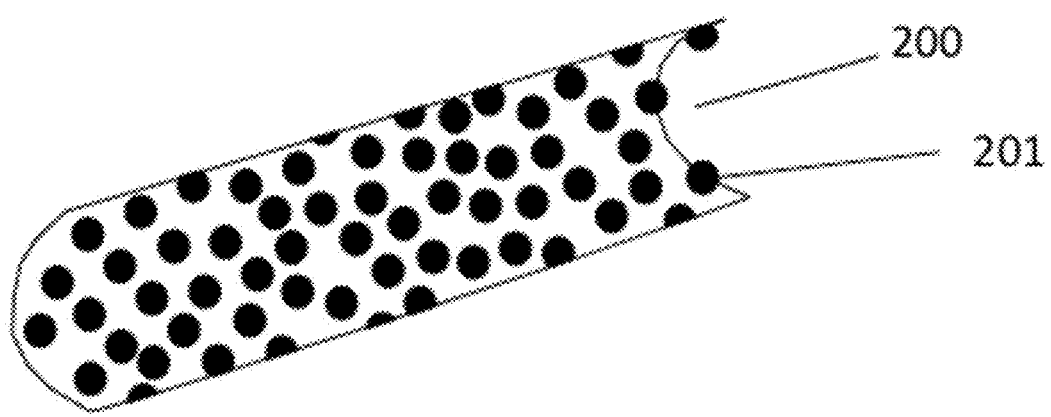
FIG. 2 is a cross section of a pore in a monolithic composite photocatalyst.

The porous network of the monolithic composite photocatalyst (FIG. 1) plays an important role in photocatalytic performance. The surface of the non-photoactive porous support 100 has photoactive nanocrystals 101 well dispersed thereon as well as in the mesopores 102, providing numerous surface reactive sites for photocatalysis to occur. The mesopores 200 (FIG. 2) have photoactive nanocrystals 201 dispersed throughout. The photoactive component comprising small, discrete photoactive nanocrystals less than 5 nm in size or photoactive nanocrystal aggregates less than 5 nm in size (imaged as white regions in the TEM image in FIG. 3) is highly effective at mineralizing organic compounds using light with wavelength of 410 nm and shorter. Modifications to the $TiO_2$ nanocrystals, including addition of cations, anions, sensitizers, light harvesters, noble metals, photocatalysts with different bandgaps, hydrogen, and the like may be used to improve performance at visible wavelengths (400-700 nm) and/or increase the residence time of light with the monolithic composite photocatalyst to increase reactivity.

The monolithic composite photocatalyst may be in any appropriate form, including powders, micron-sized beads suitable for, e.g., fluidized beds, extrudates that may be specifically designed, e.g., for reducing pressure drop in fixed and moving beds or in ebullated beds; honeycombs for minimizing pressure drops; monolith, block, brick, bar, disc, columnar, channeled block, fibrous wool or material, felt, fabric, sponge, mat, particulate, tablet, or pellet forms, or planar films or membranes.

The monolithic composite photocatalyst of the present invention satisfies a number of rigorous criteria for use in mineralizing organic species. It relies on small (less than 5 nm), discrete photoactive nanocrystals; these photoactive nanocrystals are non-agglomerated on the support or present as small agglomerates (<5 nm). The photoactive nanocrystals are present on the external surface and throughout the internal mesoporous network of the support, which means the surface area of the selected support is utilized, creating numerous reactive photocatalytic sites. The size of these pores, greater than 2 nm, is critical for efficient and facile transport of VOCs and mineralized products to and from the photoactive nanocrystal surface, improving efficiency. Importantly, the photoactive nanocrystals that reside in these pores are prepared such that their size remains less than 5 nm, despite the large size of the mesopores (up to 50 nm). The photoactive nanocrystals are fixed and immobilized on the solid support so that they cannot become airborne. The surface of the photoactive nanocrystals is substantially organic-free and available for reaction. The photoactive nanocrystals may be used as-is for light activation with wavelengths shorter than 410 nm or modified to enable activation with light wavelengths longer than 410 nm or to improve conversion efficiencies at all wavelengths. The small photoactive nanocrystal size allows creation of the electron-hole pairs throughout the photoactive nanocrystal and facile migration to the photoactive nanocrystal surface over short distances to generate reactive oxygen species. Without wishing to be bound by theory, the resulting high efficiency of the monolithic composite photocatalyst stems from the size of the active non-agglomerated photoactive nanocrystals and small agglomerates of photoactive nanocrystals (less than 5 nm), which are distributed uniformly throughout the porous network of the non-photoactive porous support, maximizing surface sites available for the formation of reactive oxygen species that will mineralize the target materials while minimizing photoactive nanocrystal surface contamination from formed intermediates. It will be appreciated that the dominant activity of catalytic particles occurs at edges, corners, and interfaces; therefore, smaller catalytic particles are an advantage because there is a larger proportion of these features per unit volume compared to larger catalytic particles. The tunable porosity of the monolithic composite photocatalyst allows for the target contaminants to be adsorbed and transferred to free reactive sites on the photoactive nanocrystal surface for mineralization, an effective strategy for overcoming mass transfer limitations at low contaminant concentrations and increasing residence time of the impurity in the immediate environment of the photoactive nanocrystals. The attrition resistance of the composite material reduces the release of fines with time, which would impact the performance of the monolithic composite photocatalyst system. When measured on beads 800 microns or smaller, an attrition rate less than 3 wt %/h may be desired for specific photocatalytic fluid purification systems where the monolithic composite photocatalyst is in a moving, fluidized, or ebullated bed. The loading of the photoactive nanocrystals on the surface of the non-photoactive porous support improves light contact with the photoactive nanocrystals throughout the monolithic composite compared to homogenous photocatalytic particles of the same size as the support, and reduces cost while maintaining high performance. The non-photoactive porous support size and shape may be tailored for accommodation in a variety of system designs including, e.g., packed, moving, ebullated, and fluidized beds.

The monolithic composite photocatalyst may also include micropores. Without wishing to be bound by theory, it is expected that the micropores will adsorb organic molecules and gaseous organic species. These impurity species would then be transferred to the photoactive nanocrystals in the mesopores and on the surface of the monolithic composite photocatalyst as photocatalytic sites become available.

The non-photoactive porous support used to make the monolithic composite photocatalyst of the disclosure may be of any suitable type, including, for example, various metal oxides, mixed metal oxides, carbons, and combinations thereof. By way of example, the non-photoactive porous support can be zirconia, alumina, silica, silica-alumina, zeolites, aluminosilicate, silicalite, carbon or combinations thereof. The porous network of the non-photoactive porous support is important for providing the necessary surface area for supporting the photoactive nanocrystals and providing ample reactivity and pore size through which impurity species can freely migrate.

In one specific embodiment, the support is an alumina with pores of at least 2 nm, e.g., preferably from 4-45 nm, most preferably from 6-40 nm, as determined from BJH analysis or NLDFT analysis of $N_2$ isotherm data collected at 77 K. It also has a $N_2$ BET surface area of at least 10 $m^2/g$, from 10-900 $m^2/g$, preferably 20-800 $m^2/g$, and more preferably 90-600 $m^2/g$. It also has pore volume of 0.2-1.5 cc/g, more preferably 0.4-1.0 cc/g.

Monolithic composite photocatalysts may be prepared using impregnation techniques in which photoactive nanocrystal precursor solutions are added to the non-photoactive porous support. The intermediate is dried and then calcined to achieve the desired crystalline phase. Repeated impregnation-drying steps may be used to increase the amount of photoactive nanocrystal precursor on the solid support. Titania precursors useful for this impregnation synthesis include titanium ethoxide, titanium propoxide, titanium isoproproxide, titanium t-butoxide, titanium nitrate, titanium oxalate, ammonium titanyl oxalate, titanium sulfate, titanium oxysulfate, titanium citrate, and ammonium titanium (IV) bis(ammonium lactato) dihydroxide. Solvents for impregnation include water, ethanol, propanol, isopropanol, dilute sulfuric acid, dilute nitric acid, and combinations thereof.

Monolithic composite photocatalysts may also be prepared from surfactant-capped nanocrystals, dissolved in solvents including water, ethanol, propanol, and isopropanol, and impregnated into the pores of the non-photoactive porous support. $TiO_2$ and titania-based photoactive nanocrystals may be prepared following a variety of wet chemical and solvothermal approaches. By varying reaction conditions including metal precursors, temperature, reaction time, solvents, and ligands, a variety of shapes (spheres, rods, bipyramids, etc.), crystalline phases, sizes, and solubilities can be achieved. Soluble, non-aggregated photoactive nanocrystals are attained by incorporating ligands that can coordinate to the surface of the nanocrystals during growth. These ligands prevent particles from aggregating, passivate surface defects, and allow for nanocrystal solubility in a variety of solvents. Dopant precursors may be added to the titania precursors in the initial stages of the reaction to facilitate their incorporation into the titania lattice. Ligands may be selected to facilitate the incorporation of the photoactive nanocrystals into the non-photoactive porous support and may include such materials as alkyl carboxylic acids and alkyl alcohols. A high-temperature calcination step may be used to remove the surface organics, leaving the monolithic composite photocatalyst substantially organic-free with less than 2% carbon residue by weight.

The properties of the monolithic composite photocatalysts of the present invention may be tailored to achieve high mineralization rates in the presence of varying amounts of relative humidity. The porosity properties of the monolithic composite photocatalyst, including surface area, pore size, and pore volume, along with its level of surface hydrophobicity may be tuned to optimize mineralization of the target chemical species under the environmental conditions of interest, including critical relative humidity and temperature ranges for, for example, storage of fresh fruits and vegetables.

A related aspect of the invention describes strategies to form the monolithic composite photocatalyst with optical absorption shifted to longer wavelengths (e.g., greater than 400 nm) to utilize visible light to stimulate the photocatalytic effect. The titania of the photoactive nanocrystals may be doped with rare earth oxides, (e.g., $TiO_2$—$CeO_2$ or any other lanthanide or combination thereof) (FIG. 4), with transition metals and transition metal oxides (e.g., Co, W, V, W, Zr, Cu, Fe Cr, Ag, etc.), or with nanoscale or microscale metal particles at the titania surface (e.g., Pt, Pd, Ag, Au, Cu, Fe, etc.). A variety of ligands may be used for the metal dopant precursor, including alkoxides, nitrates, sulfates, acetates, carbonates, and oxalates of the dopant metal additive. Similarly, non-metal dopants may be used to modify titania, including F, N, and S. Activation with visible light may also be achieved by reducing titania using, e.g., hydrogen to create sub-oxide species of titania.

A related aspect of the invention is to introduce heat to the photocatalyst in the photoreactor, to enhance thermally driven chemical reactions, which will complement the photocatalytically photon-driven chemical reactions. The introduction of heat is expected to increase the desorption rates of mineralization by-products and increase other desirable chemical reaction rates. Preferred temperatures are in the 50-150° C. range. Higher temperatures may be used transiently, for example for photocatalyst regeneration.

Inorganic sensitizers with narrower bandgaps than titania, including $C_3N_4$, $Ag_2O$, $Ag_2CO_3$, ZnO, $Cu_2O$, CuO, CdS, $Bi_2O_3$, may be coupled to titania to create a photoactive nanocrystal component that may be activated at wavelengths longer than 400 nm. The photosensitizer may also include other oxygen stoichiometries and suboxides of these compounds. Metal precursors of these inorganic sensitizers may be added during the synthesis of the photoactive titania nanocrystals on the non-photoactive porous support or they may be added following the synthesis of the monolithic composite photocatalyst. Heat treatments may be used to achieve the desired composition. Alternatively, surfactant-capped nanocrystals of these sensitizers may be prepared and impregnated in the monolithic composite photocatalyst. Heat treatments may be used to remove the organics, leaving the sensitizer-titania-based photoactive nanocrystals substantially organic-free. The sensitizer is present in the photoactive nanocrystal component at no more than 25 mole % relative to the titania, preferably no more than 15 mole % relative to the titania, and more preferably no more than 10 mole % relative to the titania. Multiple inorganic sensitizers may be used with titania to optimize the photoactivity at the desired activation wavelength.

Organic sensitizers, including porphyrins or dyes such as methylene blue, eosin Y, or rhodamine B, may also be added to enhance the visible light activity.

The monolithic composite photocatalyst, in various embodiments of the disclosure, may have characteristics comprising those shown below
  (a) greater than 90% small, discrete photoactive nanocrystals or photoactive nanocrystal aggregates with sizes less than or equal to 5 nm;
  (b) Monolithic composite photocatalyst $N_2$ BET surface area in the range 10-900 $m^2/g$;
  (c) Mesopores of the monolithic composite photocatalyst in the range 2-50 nm;
  (d) Photoactive nanocrystal loading 1-25% by mass.

The monolithic composite photocatalyst may be of widely varying types, consistent with characteristics such as those described above. In specific embodiments, the photoactive nanocrystals may be present in 1-25%, preferably 5-22%, more preferably 10-20% loading by mass. The form factor may be varied in both shape and size depending on the application. As an example, monolith, block, brick, bar, disc, columnar, honeycomb, channeled blocks, fibrous wool, felt, fabric, sponge, mat, particulate, tablet, pellet, extrudate, or bead forms may be used as the non-photoactive porous support with size ranging from microns to millimeters.

These non-photoactive porous support properties are defined by the system configuration and can be used in packed beds, moving beds, ebullated beds, fluidized beds. The monolithic composite photocatalyst may also be a powder, either directly prepared as a powder monolithic composite photocatalyst or ground from larger articles and then deposited, either mixed with another material to form a matrix or deposited directly as the monolithic composite photocatalyst on a surface. The non-photoactive porous support may be chosen to impart unique properties to the overall monolithic composite photocatalyst, including attrition resistance and crush strength resistance, creating a multifunctional material.

Figure 3:
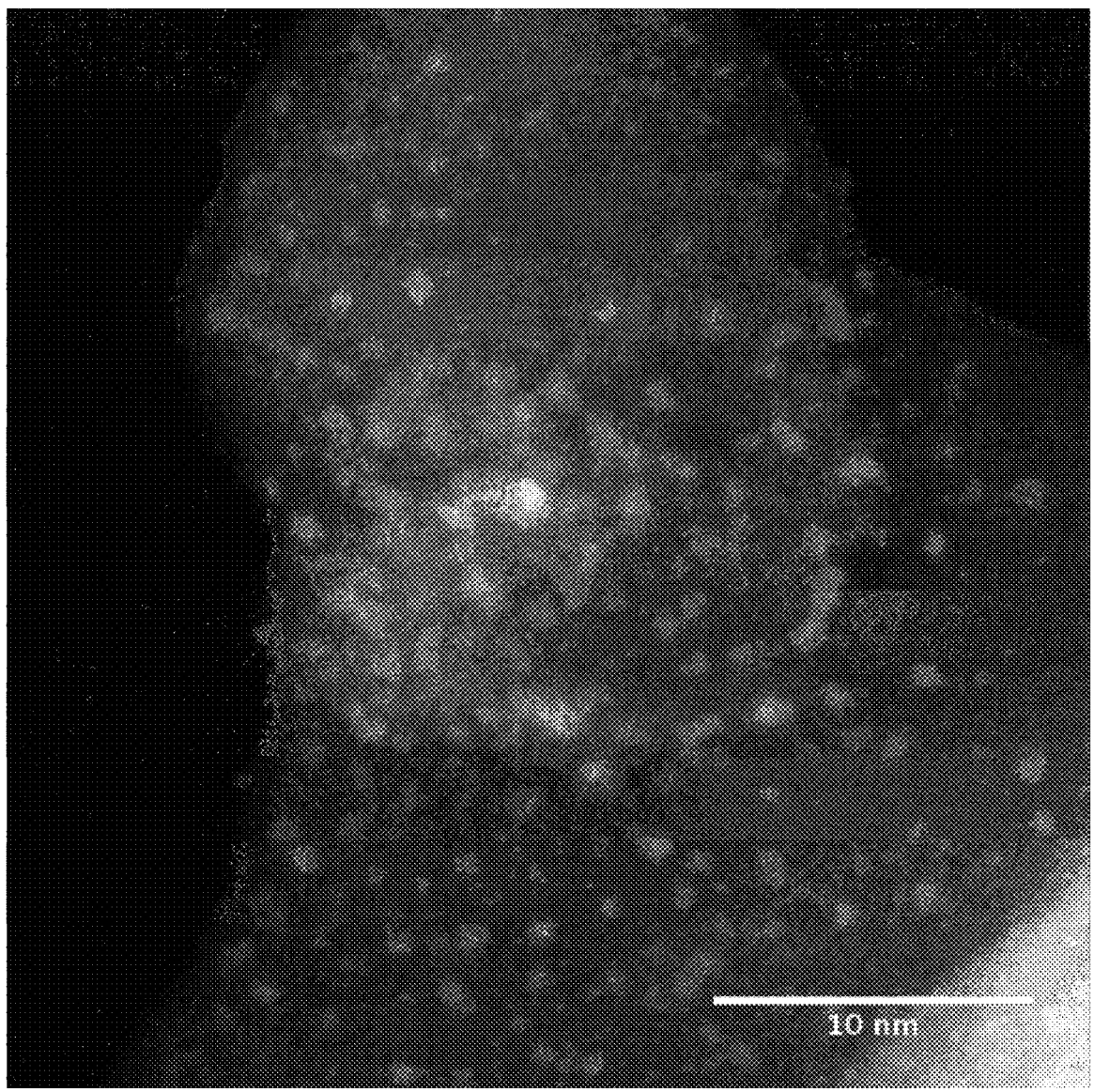
FIG. 3 shows a transmission electron microscope (TEM) image of a monolithic composite photocatalyst. The white particles are the $TiO_2$ photoactive nanocrystals distributed throughout the $Al_2O_3$ non-photoactive support (black). The scalebar is 10 nm.
Figure 4:
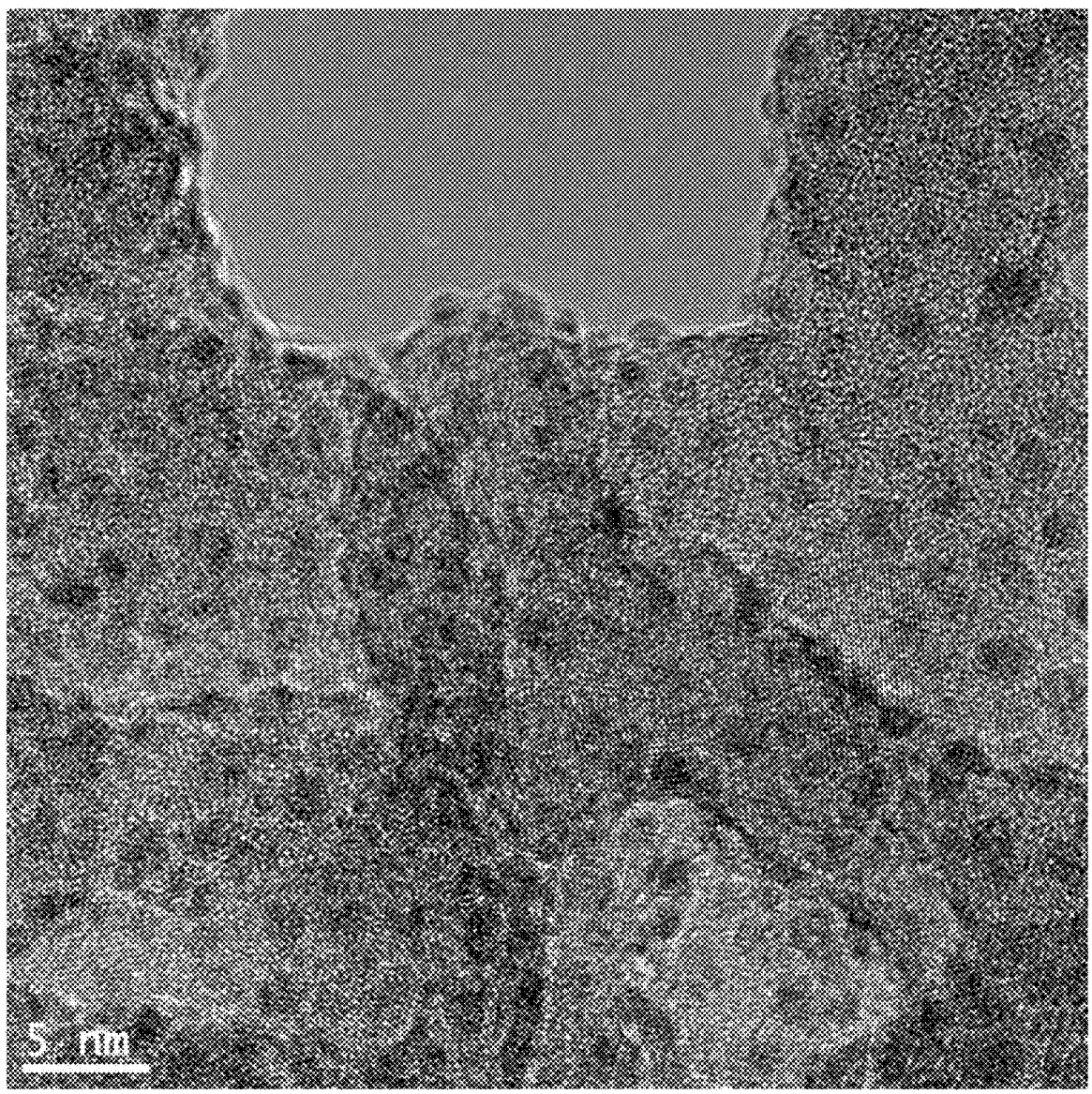
FIG. 4 shows a TEM image of a $TiO_2$—$CeO_2$ monolithic composite photocatalyst. The dark gray circles are the $TiO_2$—$CeO_2$ photoactive nanocrystals distributed throughout the $Al_2O_3$ non-photoactive support (grey). The scalebar is 5 nm.

The photoactive nanocrystals of the monolithic composite photocatalyst exist as small, discrete photoactive nanocrystals or photoactive nanocrystal aggregates adhered to the internal and external surface of the non-photoactive porous support. Greater than 90% of the discrete photoactive nanocrystals are less than 5 nm, as determined by TEM analysis (FIG. 3, FIG. 4). The nanoparticles appear as light (white) regions in FIG. 3 and as dark regions in FIG. 4, which are dark and bright field images respectively. These particles are capped with less than 2% by weight organic surfactant or other solubilizing agents, and greater than 90% of the particles exist as single, non-agglomerated photoactive nanocrystals less than 5 nm in size or small agglomerates of photoactive nanocrystals less than 5 nm in size, as determined by TEM.

Figure 5:
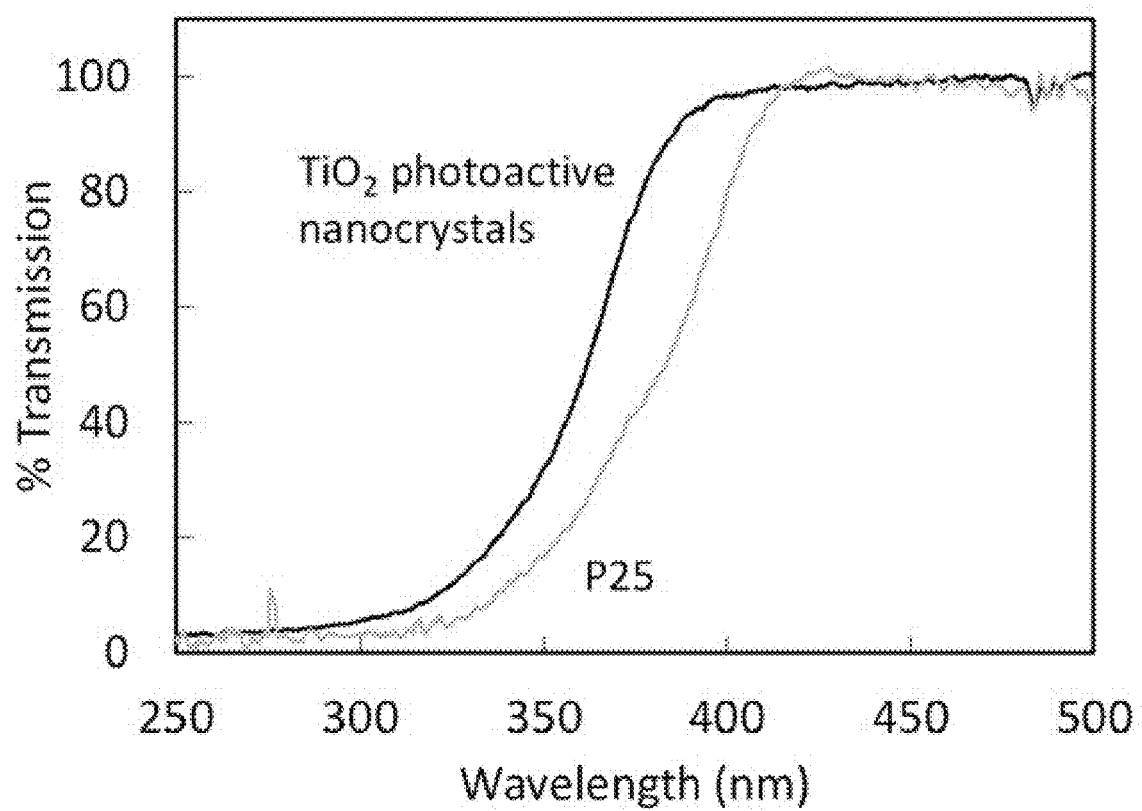
FIG. 5 shows the optical transmission of the titania photoactive nanocrystals of the monolithic composite photocatalyst, achieved using the non-photoactive porous support as the reference background (black), and P25 (gray).

For titania particles in this size regime, smaller than 5 nm in size, the bulk bandgap shifts to higher energy as the particle size decreases. The optical transmission of the titania photoactive nanocrystals of the monolithic composite photocatalyst, referenced to the non-photoactive porous support, is shown in FIG. 5 along with the bulk titania photocatalyst, P25. The transmission curve of the titania photoactive nanocrystals of the monolithic composite photocatalyst, whose TEM image is shown in FIG. 3, is shifted to higher energy, consistent with the particle size (<5 nm) depicted in the TEM image.

Figure 6:
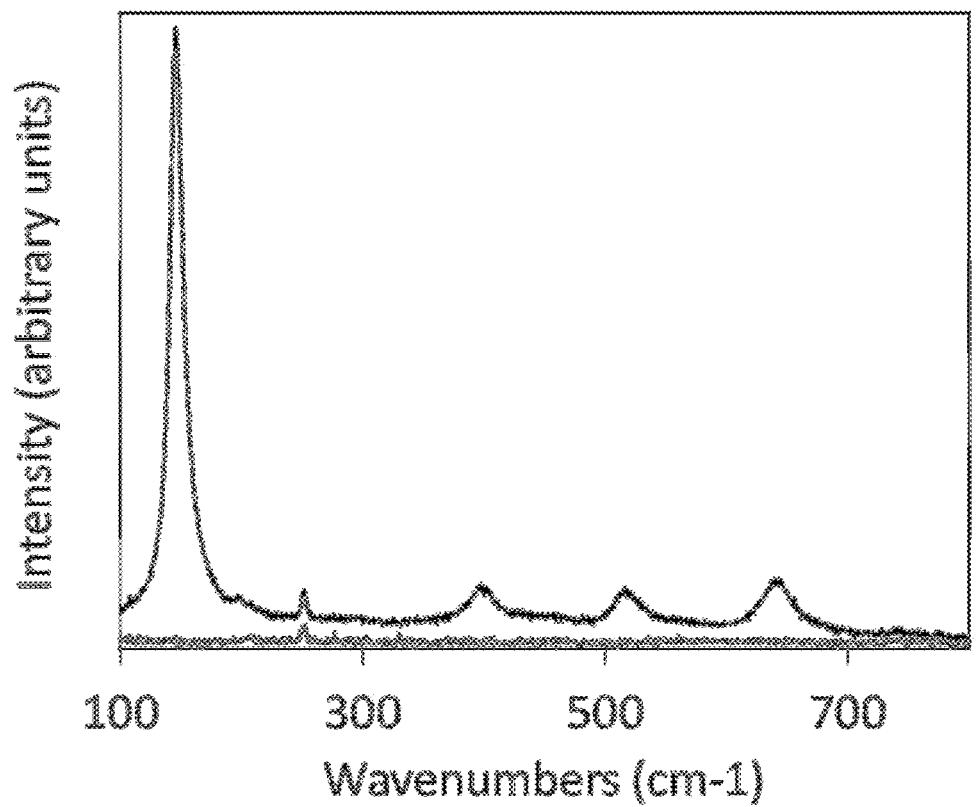
FIG. 6 shows the Raman spectra of a monolithic composite photocatalyst comprising primarily anatase $TiO_2$ photoactive nanocrystals on a non-photoactive porous support (black) and the non-photoactive porous support without $TiO_2$ photoactive nanocrystals (gray) for comparison.

It is known that the anatase phase of titania plays an important role for efficient photocatalytic behavior in titania bulk photocatalysts. Raman spectroscopy and x-ray diffraction are common analytical approaches for evaluating the phase of titania, and Raman, particularly, provides an accurate assignment of the titania phase in the monolithic composite photocatalysts (FIG. 6) and allows it to be resolved independent of the rutile and amorphous components. Greater than 75% of the titania of the photoactive nanocrystals of the monolithic composite photocatalysts is in the anatase crystal phase for efficient photocatalytic reactions.

Another aspect of the invention is the regeneration of the monolithic composite photocatalysts. Photocatalyst fouling may occur through a number of pathways, including the adsorption of incompletely mineralized by-products onto the monolithic composite photocatalyst. Monolithic composite photocatalysts may be regenerated for re-use by irradiating the monolithic composite photocatalyst in the presence of a humidified air stream. Alternatively, heat treatments may be used to drive off the adsorbed species. Monolithic composite photocatalyst surfaces may be re-primed with hydroxyl groups using wet etching techniques, including peroxide, acid, or base treatments.

A related aspect of the invention is the application of these monolithic composite photocatalysts for water purification. Unlike bulk photocatalysts that exists primarily as powders and suffer severe attrition when supported on a substrate, the monolithic composite photocatalysts are resistant to attrition and can exist in a variety of bead or monolithic forms, allowing for easy, clean, and facile removal from the purified water.

A related aspect of the invention is the application of these monolithic composite photocatalysts to achieve chemical transformations typically achieved with traditional thermal catalysts at high pressures and high temperatures. The use of the monolithic composite photocatalysts described in this disclosure will promote these transformations at lower temperatures and/or lower pressures than typically employed. The properties of the monolithic composite photocatalyst and the reaction conditions employed may be tailored to achieve the desired product in high yield with high selectivity. Reaction conditions can include light alone or in combination with heat and or/pressure to achieve the desired outcome. Reaction rates may be optimized for a variety of environmental conditions, including moderate to high humidity environments (>40% relative humidity), by tuning the surface properties (for example, surface hydrophobicity) and/or porosity characteristics of the monolithic composite photocatalyst. Examples of transformations catalyzed with the monolithic composite photocatalysts described herein include $CO_2$ to methanol and/or methane, oxidation of hydrocarbons and alcohols, epoxidation of alkenes, hydroxylation of aromatics, hydrogenation, conversion of NO to $N_2$ and $O_2$, and C—H activation reactions, particularly for light hydrocarbons.

A related aspect of the invention is the fabrication of photocatalytic surfaces by incorporation of the subject monolithic composite photocatalyst, a powder, into a liquid organic or inorganic matrix material. The monolithic composite photocatalyst may also be dispersed into a powdered organic or inorganic matrix material, or mixtures of organic and inorganic matrix materials that are then applied to substrates and cured to form a robust mixture of the monolithic composite and matrix as a coating.

The monolithic composite photocatalyst of the present disclosure satisfies a number of rigorous criteria for use in killing pathogens on surfaces. It relies on small (less than 5 nm size), non-agglomerated or small agglomerate (less than 5 nm size) $TiO_2$ or $TiO_2$-based photoactive nanocrystals. The photoactive nanocrystals are immobilized on a non-photoactive porous support so that they cannot become airborne. The photoactive nanocrystals may be used as-is for light activation with wavelengths shorter than 410 nm or modified to enable activation with light wavelengths longer than 410 nm or improved conversion efficiencies at all wavelengths, such as with inorganic sensitizers. Without wishing to be bound by theory, the resulting high efficiency of the monolithic composite photocatalyst stems from the size of the photoactive nanocrystals (less than 5 nm), which are present as non-agglomerated particles or small agglomerates (less than 5 nm) and distributed uniformly throughout the surface of the powder, maximizing sites available for the formation of reactive oxygen species that will kill the target pathogens. The homogeneity of the photoactive nanocrystals throughout the support reduces the likelihood of agglomeration of photoactive nanocrystals on the surface. Once incorporated into the matrix material, the photoactive nanocrystal particles will be in limited contact with the coating and will most often be surrounded by the non-photoactive porous support material, reducing the chance for decomposition of the coating with time and extending the lifetime of the coating. The properties of the non-photoactive porous support may be selected to impart important characteristics to the coatings, including hardness and strength.

The matrix may be either inorganic- or organic-based. Examples of inorganic matrix materials are silica, alumina, or titania film materials. Organic matrix materials may be rigid materials such as rigid epoxies, polyurethanes, polycarbonates, polypropylenes, polyesters, epoxy modified polyesters, thermoplastics (e.g., nylon, PET), or pliable materials such as silicones or flexible epoxies. Organic matrix materials may also comprise combinations of these constituent materials. These matrix materials may be deposited as thin coatings through, e.g., spray coating, spin coating, powder coating, dip coating, drop coating, and roll-to-roll printing. The matrix/monolithic composite photocatalyst may also be prepared as 3D-printed articles such as doorknobs, touch screens, light switches, and the like.

Alternatively, the monolithic composite photocatalyst may be deposited directly on a support such as, e.g., a glass with a low melting temperature, as small particles or powders and heated to adhere the particles to the support. The geometry of the support may be varied and can include planar substrates, rods, cylinders, fibers, helical elements, and the like. The monolithic composite photocatalyst may also be deposited directly on a coated support such that the monolithic composite photocatalyst forms the top layer of the coating and is adhered firmly to the underlying coating.

Mixtures of the monolithic composite photocatalyst with dry organic and inorganic materials may be applied to substrates using powder coating techniques. Examples of inorganic matrix materials are silica, alumina, titania, silicon carbide, other carbides, nitrides and pigment materials. Organic matrix materials may be rigid materials such as rigid epoxies, polyurethanes, polycarbonates, polypropylenes, polyesters, epoxy modified polyesters, thermoplastics (e.g., nylon, PET), or pliable materials such as silicones or flexible epoxies. Organic matrix materials may also comprise combinations of these constituent materials. Powder coating may be carried out by electrostatically charging the particles and spraying them onto a grounded conductive substrate, e.g., steel, aluminum, and the like. In cases where the substrate is non-conductive, a conductive undercoat may be used to attract the electrostatically charged particles. After spraying, the coating may be cured at elevated temperature between 150-300° C., preferably between 200-250° C., to create a robust layer that resists wear.

The monolithic composite photocatalyst loading levels within the matrix material may be varied to achieve optimum performance (0.1-40 wt %). Once deposited, the photocatalyst surfaces may be activated with wet-etchants, including peroxide, to enhance the surface hydroxyl groups necessary for forming the reactive oxygen species critical for photocatalysis. These etchants may be applied during routine cleaning/wipe-down cycles as an approach for reinvigorating and optimizing the photocatalysis efficiency. The surfaces may also be wiped down with traditional cleaning products.

One embodiment involves the deposition of monolithic-composite-photocatalyst-containing matrix materials onto hard surfaces, including those found in hospital rooms and operating rooms as well as on instrumentation, which includes surgical instruments, catheters, and other non-implantable items that have the potential to carry bacteria and viruses. Monolithic composite photocatalysts with suitable inorganic or organic matrix materials, including sol-gel, spin-on-glass, siloxanes, polyurethanes, and other appropriate materials, may be deposited onto these substrates using a variety of techniques, including spray-coating, printing, powder coating, spin-coating, dip-coating, additive manufacturing (i.e., 3D printing), extrusions, printing, incorporation on fibers, etc. This matrix may also be deposited on glass surfaces or plastic coatings (e.g., 150 μm polyethylene terephthalate (PET)) that will be applied to the surface of interest as a second step. The matrix must meet the durability requirements for effective functioning, including robustness. In one example, an inorganic polymer matrix such as a silica sol-gel is used. Silica sols can withstand degradation from reactive oxygen species. Curing temperatures are low, at less than 120° C., which allow compatibility with plastic substrates. Titania sols have been successfully deposited onto biomedical devices for photocatalytic antimicrobial testing.

Matrix materials that have high hardness values will impart good wear resistance to the film. Additionally, the non-photoactive porous support in the monolithic composite photocatalyst may also be exploited for its properties, including, in the case of $Al_2O_3$, hardness. It is expected that $TiO_2$ (Mohs hardness=6) and $Al_2O_3$ (Mohs hardness=9) will provide high durability. Very small amounts of $Al_2O_3$ (<0.5%) have a large effect on the wear resistance of polymer films like epoxies. Additional additives that can enhance the mechanical properties of the films include silica, refractory oxides, carbides, nitrides.

These monolithic composite photocatalysts are typically insoluble in many solvents but may be dispersed in a variety of ways, including through milling and shear mixing. High-speed shear mixing mechanically shears large particles, reducing their size. As they become smaller, the monolithic composite photocatalyst is more easily dispersed. These monolithic composite photocatalysts may be added to spin-on-glasses, siloxanes, polyurethanes, etc., and the monolithic composite photocatalyst matrix material deposited using various spin coating, spraying, powder coating, dip coating, and 3D printing approaches.

Previous work has shown that UV light (365 nm) can degrade organics, but photo-degradation is not an expected outcome with visible light activation. The incorporation of monolithic composite photocatalysts into film matrix materials that contain organic species, including, e.g., siloxanes (silicones) and polyurethanes, must also be accomplished without degrading the organic components to a degree that affects the film wear-resistance during photocatalytic activity (i.e., the generation of reactive oxygen species). Use of monolithic composite photocatalysts will provide a barrier layer between the photocatalyst and the organic film. Further, dispersing minimum concentrations of the monolithic composite photocatalyst homogeneously throughout the film (accomplished by achieving high solubility through, e.g., shear mixing) is critical for preserving film properties.

Visible-light-activated monolithic composite photocatalysts, prepared as described in this invention, may be employed to impart antimicrobial properties to a variety of touch surfaces. Examples include touch screens, smart phone covers, elevator buttons, light switches and doorknobs. These items may be illuminated by ambient light or by lights provided internally for various functionality, e.g., backlighting of a smart phone screen, indicator lighting in switches, etc. The light source may be optionally programed to come on at intervals.

Another implementation may be the use of visible-light-activated monolithic composite photocatalyst in wound dressings. In this application, antimicrobial properties may be achieved without the use of antibiotics or materials toxic to the body. The dressing may be lighted externally or may have an internal light source. An example of the latter is a photoluminescent layer in proximity to the monolithic composite photocatalytic layer in the bandage. The illuminating layer could be a two-component mixture that is activated by breaking a barrier layer between the two materials that react to form light.

The Inventions summarized above are described and illustrated in several examples.

Example 1

A sample of monolithic composite photocatalyst (150 mg) was loaded in a 10 mm outer diameter quartz tube. Titania photoactive nanocrystals are 1-2 nm in size and immobilized on an alumina non-photoactive porous support. The monolithic composite photocatalyst has a surface area in the range 50-400 $m^2/g$, pores in the 6-40 nm range, and pore volume in the 0.4-0.8 cc/g range. The photoactive nanocrystal loading is 10-20%, and the titania was greater than 80% anatase.

The photocatalytic efficiency was tested in a single pass reactor. The loaded sample of monolithic composite photocatalyst was packed between quartz wool or stainless steel mesh into a 6.35 mm inner diameter, UV-transparent reactor tube. High packing density was achieved by gently tapping the side of the tube with the metal rod. The reactor was placed ca. 1 cm away from a strip of LED lights whose maximum emission was 365, 385, or 405 nm. The maximum radiant flux of each light is 1400, 1450, or 1450 mW, respectively. Lights were typically operated between 15-50% full power using a variable power supply. The LED strip contains 22 LEDs, but only 1-7 directly illuminated the catalyst bed. Gas was supplied through three calibrated mass flow controllers (MFCs). One MFC delivered toluene from a 10 ppm toluene cylinder balanced with dry air. A second MFC was used to dilute toluene using ultra-dry air. Toluene concentrations of 500-2500 ppb were used. The third MFC bubbled ultra-dry air through deionized water to provide humid air measured by an in-line humidity sensor. The system operated at 23% relative humidity. An in-line temperature sensor measured the temperature of the incoming gas at 23° C. Total flow rates through the reactor were 550-650 sccm. Total VOC concentration in the gas stream was monitored using a photoionization detector (Honeywell ppbRAE 3000).

Figure 7:
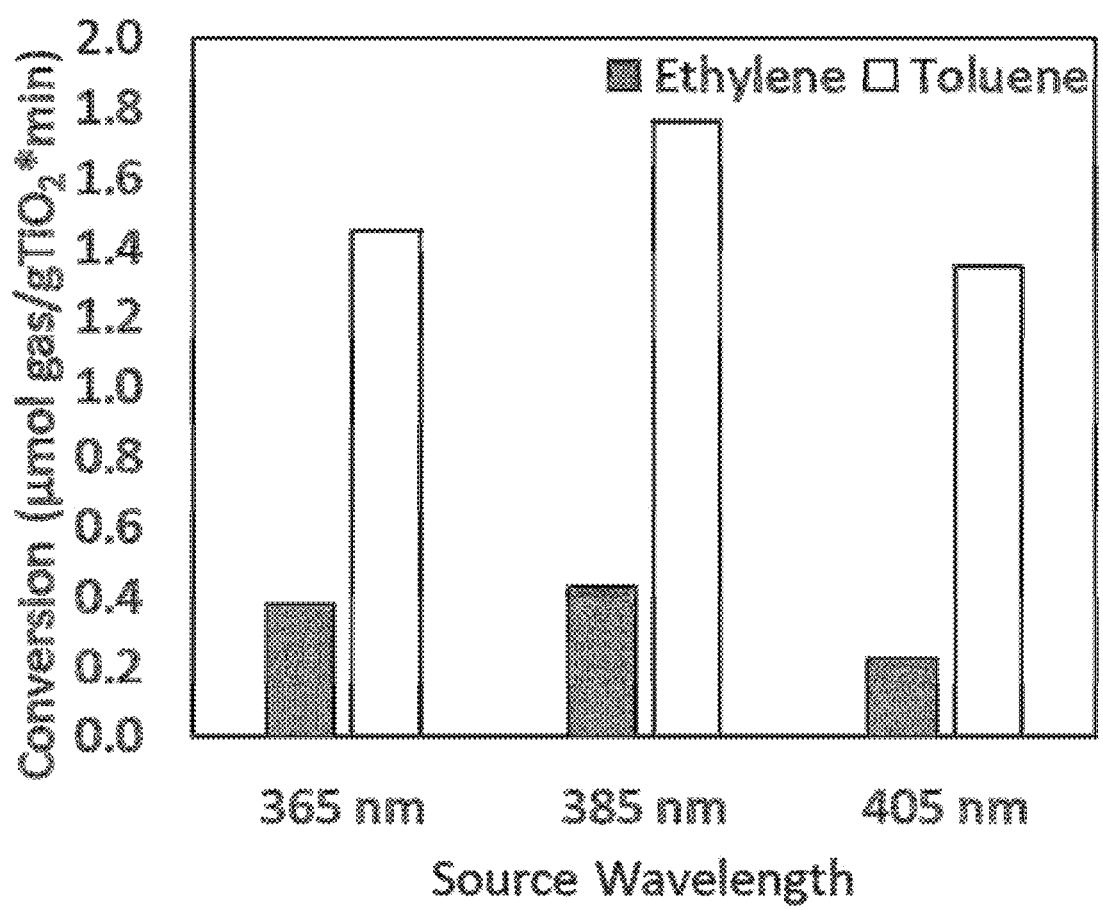
FIG. 7 shows ethylene and toluene conversion by a monolithic composite photocatalyst as a function of illumination wavelength.

Toluene conversion was measured in six steps. (1) The detector was 2-point calibrated by passing a known quantity of the target gas through an empty tube and ultrapure air through the same tube. (2) A baseline detector reading was measured by passing ultrapure air through the catalyst reactor for 1-5 minutes. (3) The desired toluene concentration was passed through the reactor until a steady reading on the ppbRAE was achieved, usually 10-30 minutes. (4) The LEDs were turned on to the desired power from 5 minutes to 24 hours, and the drop in the ppbRAE reading corresponded to the fraction of toluene that degraded over the monolithic composite photocatalyst, the ppbRAE does not detect $CO_2$ from the reaction. Experiments without the photoactive $TiO_2$ nanocrystals and LEDs showed no degradation of toluene, indicating the photoactive component was necessary for reaction. Degradation rates of toluene using this setup ranged from 0.05-2.0 μmol toluene*g $TiO_2^-$ 1*$min^{-1}$ as plotted in FIG. 7. Steps 2 and 1 were then repeated to ensure there were no changes in the ppbRAE response over the length of the experiment. All data was logged using the internal ppbRAE datalogger.

Example 2

A sample monolithic composite photocatalyst (200 mg) with properties as described in the previous example was loaded into the 10 mm diameter quartz tube and analyzed as described in the previous example. Ethylene was supplied from a 10 ppm cylinder balanced with dry air. Initial ethylene concentrations in the reactor ranged from 500-2500 ppb. For ethylene detection, the ppbRAE was recalibrated to known quantities of ethylene through a blank tube. Ethylene conversion using this setup ranged from 0.1-0.7 μmol ethylene*g $TiO_2^{-1}$*$min^{-1}$, as plotted in FIG. 7.

Example 3

A sample of monolithic composite photocatalyst with properties described in the previous example was ground in a mortar and pestle (75 mg). The powder was added to 1.5 mL water, and the slurry was sonicated for 40 minutes. A glass substrate (1"×2") was prepared by a dilute nitric acid wash followed by a piranha etch wash, rinsed with water, and dried in a stream of nitrogen. The monolithic composite photocatalyst in water was drop-cast onto the surface of the substrate, and the sample was placed into an oven at 120° C. for 2 hours. The substrate was then heated to 300° C. for 1 hour and cooled. A similar procedure was used to deposit a film of the non-photoactive porous support.

Figure 8:
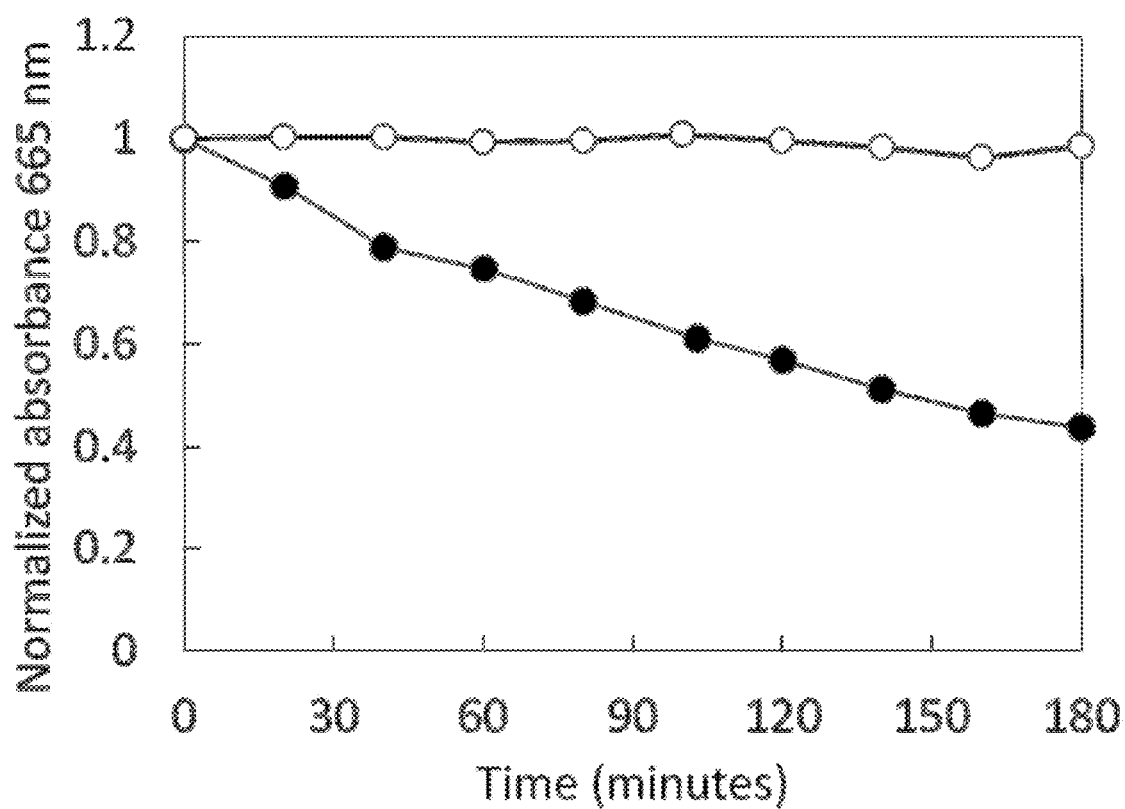
FIG. 8 shows conversion of methylene blue in water by a monolithic composite photocatalyst (black circles) and the non-photoactive porous support only (open circles) with 365 nm LED illumination.

A custom reactor was loaded with 35 mL of a 2.01×10$^{-5}$ M solution of methylene blue in water. The substrate with monolithic composite photocatalyst described above was placed into the custom reactor where it was supported on rails above a stir bar. A fiberoptic dip probe was inserted next to the slide and a glass plate was placed on top of the reactor to prevent evaporation. UV light (365 nm) was supplied from 1-4 star-board LEDs with a maximum radiant flux of 2400 mW for each source mounted to an aluminum plate. The LEDs were placed 31 cm above the methylene blue reservoir to prevent a temperature increase of the solution and were operated so to give a uniform irradiance of the sample at 1 mW/cm$^2$. Methylene blue degradation was measured as the decay in the adsorption spectra of methylene blue as a function of irradiation time from the 365 nm light source over 180 minutes. Photooxidation from the dip probe light sourced did not contribute to the degradation rate. The degradation of methylene blue over time is shown as the change in the absorbance at 665 nm with time, as depicted in FIG. 8 with black circles. The behavior of the non-photoactive porous support only is shown for comparison (open circles).

Example 4

Figure 9:
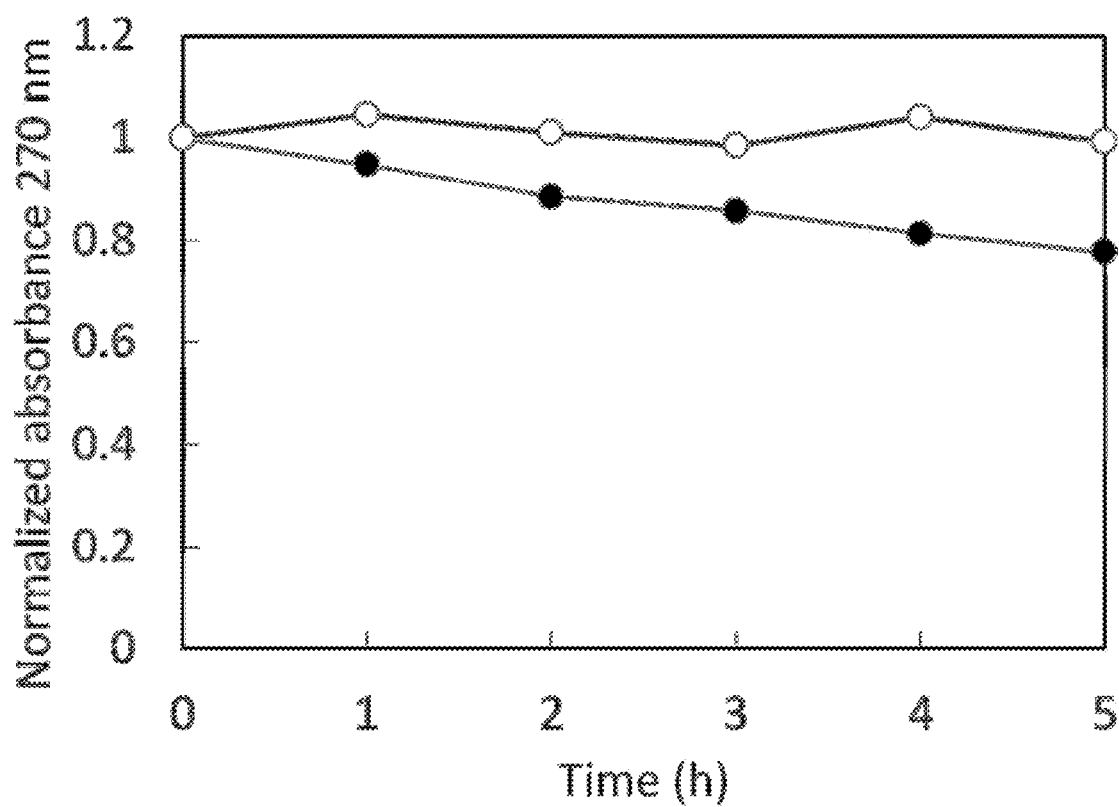
FIG. 9 shows conversion of phenol in water by a monolithic composite photocatalyst (black circles) and the non-photoactive porous support only (open circles) with 405 nm LED illumination.

A sample of monolithic composite photocatalyst (50 mg) was placed in a 2 dram vial. The photoactive nanocrystals of this monolithic composite photocatalyst comprise titania with a $Bi_2O_3$ sensitizer at less than 10 mol % relative to the titania. The titania-$Bi_2O_3$ photoactive nanocrystals are on an alumina non-photoactive porous support. The monolithic composite photocatalyst has a surface area in the range 50-400 m$^2$/g, pores in the 6-40 nm range, and pore volume in the 0.4-0.8 cc/g range. The photoactive nanocrystal loading is 10-20%, and the titania is greater than 80% anatase. To the monolithic composite photocatalyst was added 5 mL 5.3×10$^{-4}$ M phenol in water. The sample vial was place horizontally on an orbital shaker set for 100 rpm. The sample vial was illuminated with 405 nm LEDs operated to provide the sample with a uniform irradiance of 12.2 mW/cm$^2$. Phenol degradation was measured as the decay in the adsorption spectra of phenol as a function of irradiation time from the 405 nm light source over 6 hours. The degradation of phenol over time is shown as the change in the absorbance at 270 nm with time, as depicted in FIG. 9 by the black circles. The behavior of the non-photoactive porous support only is shown for comparison (open circles).

Example 5

A sample of monolithic composite photocatalyst with properties described in Example 3 was ground in a mortar and pestle (75 mg). The powder was added to 1.5 mL water, and the slurry was sonicated for 40 minutes. A glass substrate (1"×1.5") was prepared by a dilute nitric acid wash followed by a piranha etch wash, rinsed with water, and dried in a stream of nitrogen. The monolithic composite photocatalyst in water was drop-cast onto the surface of the substrate, and the sample was placed into an oven at 120° C. for 2 hours. The substrate was then heated to 300° C. for 1 hour and cooled.

Figure 10:
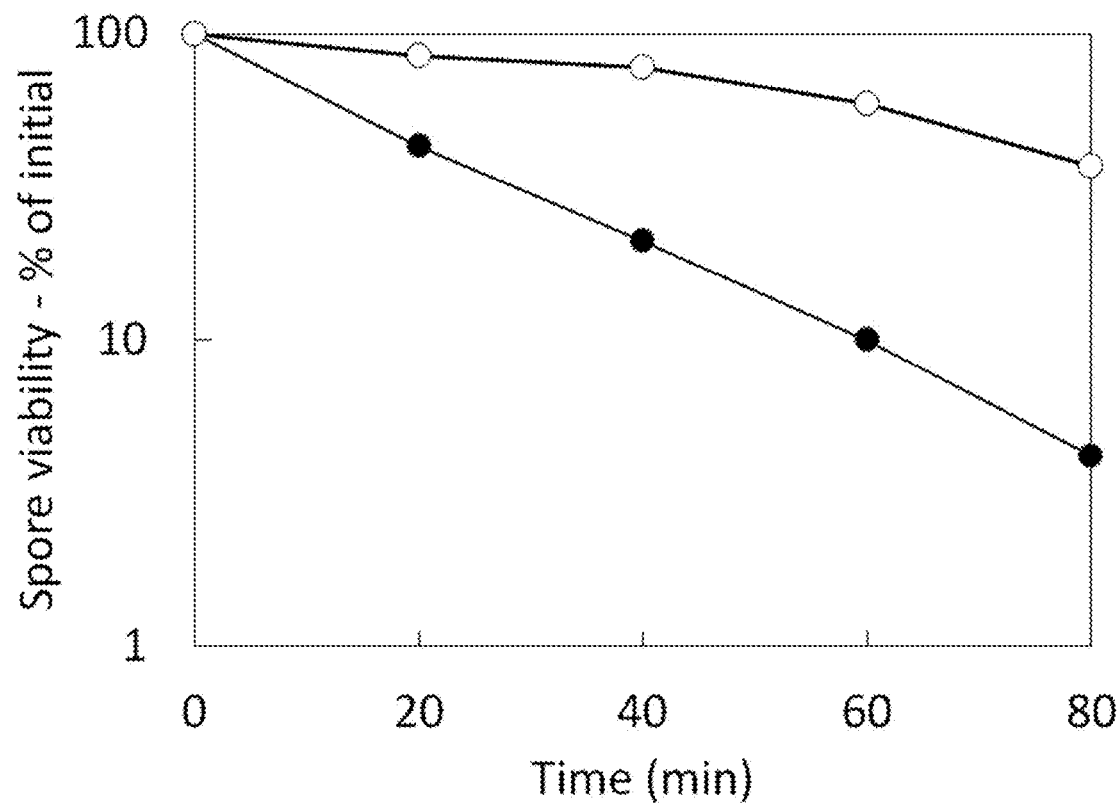
FIG. 10 shows the sporicidal effect of a monolithic composite photocatalyst at 365 nm on *Bacillus subtilis*, PS533 (black circles) and the results from illumination of the non-photoactive porous support only (open circles).

Highly purified dormant spores of a 168 strain of *Bacillus subtilis*, PS533, which carries a plasmid providing resistance to kanamycin (10 μg/mL), were suspended in water at ca. 1.5×10$^8$ colony forming units (CFUs)/mL. Approximately 1.5 mL of this suspension was applied to the prepared slides. The slides with the spores were then exposed at 23° C. to 365 nm irradiation approximately 6 cm from a single LED operating at a radiant flux of 2750 mW. At various times aliquots (ca. 20 μL) of the irradiated samples were diluted 1/10 in water and then serially diluted further. 10 μL aliquots of various dilutions were then spotted in duplicate in a grid on rich medium (L broth) agar plates containing 10 μg/mL kanamycin. After liquid was absorbed into the plates, they were incubated 16-36 h at 30-37° C., ensuring that individual colonies never got large enough to run together. However, no colonies appeared after ca 30 h. Finally, colonies were counted for irradiated samples with and without the photoactive nanocrystals, and CFUs, and thus the percentage of spore viability at various irradiation times, were calculated. An example of spore killing with the monolithic composite photocatalyst (black circles) and with the non-photoactive porous support only (open circles) is shown in FIG. 10.

The subject invention may be embodied in the forgoing examples that are by no means restrictive, but intended to illustrate the invention. Any embodiment herein described may be combined with any other embodiment described, in particular different physical and chemical formulations of the monolithic composite photocatalysts.

What is claimed is:

1. A monolithic composite photocatalyst, comprising titania or titania-based photoactive nanocrystals and a non-photoactive porous support for the photoactive nanocrystals, said monolithic composite photocatalyst having all of the following characteristics: (a) greater than 90% discrete photoactive nanocrystals or photoactive nanocrystal aggregates have a size less than or equal to 5 nm; (b) monolithic composite photocatalyst $N_2$ BET surface area is in the range 10-900 m$^2$/g; and (c) mesopores having pores in the size range of 2-50 nm.

2. The monolithic composite photocatalyst of claim 1, wherein photoactive nanocrystal loading in the monolithic composite photocatalyst is 1-25% by mass.

3. The monolithic composite photocatalyst of claim 1, wherein photoactive nanocrystal loading in the monolithic composite photocatalyst is 10-20% by mass.

4. The monolithic composite photocatalyst of claim 1, wherein the $N_2$ BET surface area is in the range 90-600 m$^2$/g.

5. The monolithic composite photocatalyst of claim 1, wherein the mesopores are in the range 6-40 nm.

6. The monolithic composite photocatalyst of claim 1, wherein the photoactive nanocrystal component is at least 80% titania by mass.

7. The monolithic composite photocatalyst of claim 1, wherein micropores are present in the range 0.5-2 nm.

8. The monolithic composite photocatalyst of claim 1, wherein the total pore volume is 0.1-1.5 cc/g.

9. The monolithic composite photocatalyst of claim 1, wherein greater than 75% of the titania photoactive component is the anatase crystal phase.

10. The monolithic composite photocatalyst of claim 1, comprising less than 2% carbon residue by weight.

11. The monolithic composite photocatalyst of claim 1, comprising spheres less than 800 micron with attrition less than 3 wt %/h.

12. The monolithic composite photocatalyst of claim 1, which is activated with light at wavelengths shorter than 410 nm.

13. The monolithic composite photocatalyst of claim 1, which is activated with light at wavelengths longer than 410 nm.

14. The monolithic composite photocatalyst of claim 1, wherein the non-photoactive porous support component is selected from the group consisting of alumina, silica, zirconia, zeolite, silicalite, silica-alumina, aluminosilicate, and combinations thereof.

15. The monolithic composite photocatalyst of claim 1, having a shape of monolith, block, brick, bar, disc, columnar, honeycomb, channeled block, fibrous wool, felt, fabric, sponge, mat, particulate, tablet, pellet, extrudate, or bead forms.

16. The monolithic composite photocatalyst of claim 1, wherein the titania photoactive nanocrystals are modified with an element chosen from the groups of lanthanides, noble metals, or non-metals, thereby improving the efficiency of light activation at wavelengths longer than 400 nm.

17. A monolithic composite photocatalyst, comprising photoactive nanocrystals and a non-photoactive porous support for the photoactive nanocrystals, said photoactive nanocrystals comprising titania or titania-based nanocrystals and an inorganic sensitizer, and said monolithic composite photocatalyst having all of the following characteristics: (a) greater than 90% discrete photoactive nanocrystals or photoactive nanocrystal aggregates have a size less than or equal to 5 nm; (b) monolithic composite photocatalyst $N_2$ BET surface area is in the range 10-900 $m^2/g$; and (c) mesopore size in the range 2-50 nm.

18. The monolithic composite photocatalyst of claim 17, wherein the photoactive nanocrystals comprise titania and the inorganic sensitizer $Bi_2O_3$, $Ag_2O$ or CuO.

19. The monolithic composite photocatalyst of claim 17, wherein the photoactive nanocrystals comprise titania and more than one inorganic sensitizer.

20. The monolithic composite photocatalyst of claim 17, wherein the sensitizer is present in the photoactive nanocrystal component at less than 25 mole % relative to the titania.

21. A photocatalytic fluid purification system comprising a monolithic composite photocatalyst in a photoreactor, wherein the monolithic composite photocatalyst comprises titania or titania-based photoactive nanocrystals and a non-photoactive porous support for the photoactive nanocrystals, said monolithic composite photocatalyst having all of the following characteristics: (a) greater than 90% discrete photoactive nanocrystals or photoactive nanocrystal aggregates have a size less than or equal to 5 nm; (b) monolithic composite photocatalyst $N_2$ BET surface area is in the range 10-900 $m^2/g$; and (c) mesopores in the range 2-50 nm, and said photocatalytic purification system is configured for contacting a portion of the monolithic composite photocatalyst with an impurity-containing fluid stream in a location where the portion of the monolithic composite photocatalyst is illuminated with UV or visible-light.

22. The photocatalytic fluid purification system of claim 21, further utilizing thermal energy in addition to UV or visible-light photocatalytic illumination to affect or enhance mineralization or chemical transformations.

23. The photocatalytic fluid purification system of claim 21, further incorporating a photocatalyst regeneration capability.

24. The photocatalytic fluid purification system of claim 21, further utilizing a packed, moving, ebullated or fluidized bed.

25. An antimicrobial surface, comprising a polymer matrix and monolithic composite photocatalyst, said monolithic composite photocatalyst comprising photoactive nanocrystals and a non-photoactive porous support for the photoactive nanocrystals, said photoactive nanocrystals comprising titania or titania-based nanocrystals and an inorganic sensitizer, and said monolithic composite photocatalyst having all of the following characteristics: (a) greater than 90% discrete photoactive nanocrystals or photoactive nanocrystal aggregates have a size less than or equal to 5 nm; (b) monolithic composite photocatalyst $N_2$ BET surface area is in the range 10-900 $m^2/g$; and (c) mesopore size in the range 2-50 nm.

* * * * *

UNITED STATES PATENT AND TRADEMARK OFFICE
CERTIFICATE OF CORRECTION

PATENT NO. : 11,241,671 B2  
APPLICATION NO. : 16/680495  
DATED : February 8, 2022  
INVENTOR(S) : Melissa A. Petruska et al.

Page 1 of 1

It is certified that error appears in the above-identified patent and that said Letters Patent is hereby corrected as shown below:

On the Title Page

Please remove under item (63) "Related Application Data", and replace it with:
"Continuation in part of application No. 16/212,663, filed on Dec. 6, 2018, now Pat. No. 11,052,385.
Continuation in part of application No. 16/147,536, filed on Sept. 28, 2018."

Add the following to item (60), relating to Provisional Applications:
"Provisional application No. 62/760,428, filed on Nov. 13, 2018.
Provisional application No. 62/595,261, filed on Dec. 6, 2017.
Provisional application No. 62/564,408, filed on Sept. 28, 2017."

Signed and Sealed this  
Tenth Day of September, 2024

Katherine Kelly Vidal  
*Director of the United States Patent and Trademark Office*